United States Patent
Hanovich et al.

(10) Patent No.: US 9,584,755 B2
(45) Date of Patent: Feb. 28, 2017

(54) ENDOSCOPE WITH HIGH DEFINITION VIDEO RECORDER/PLAYER

(71) Applicant: GYRUS ACMI, INC., Southborough, MA (US)

(72) Inventors: Tal Hanovich, Kiryat Biyalik (IL); Shai Finkman, Haifa (IL); Dmitri Gorlik, Kiryat Motzkin (IL); Igor Kagan, Kiryat Biyalik (IL)

(73) Assignee: GYRUS ACMI, INC., Southborough, MA (US)

( * ) Notice: Subject to any disclaimer, the term of this patent is extended or adjusted under 35 U.S.C. 154(b) by 0 days.

(21) Appl. No.: 15/177,351

(22) Filed: Jun. 9, 2016

(65) Prior Publication Data
US 2016/0286160 A1 Sep. 29, 2016

Related U.S. Application Data

(62) Division of application No. 13/760,086, filed on Feb. 6, 2013, now Pat. No. 9,392,214.

(51) Int. Cl.
| | |
|---|---|
| H04N 7/01 | (2006.01) |
| H04N 7/18 | (2006.01) |
| H04N 5/77 | (2006.01) |
| H04N 9/804 | (2006.01) |
| A61B 1/00 | (2006.01) |
| A61B 1/04 | (2006.01) |
| H04N 7/015 | (2006.01) |
| H04N 5/225 | (2006.01) |

(52) U.S. Cl.
CPC ......... *H04N 7/0125* (2013.01); *A61B 1/0002* (2013.01); *A61B 1/00009* (2013.01); *A61B 1/00011* (2013.01); *A61B 1/04* (2013.01); *H04N 5/77* (2013.01); *H04N 7/185* (2013.01); *H04N 9/8042* (2013.01); *H04N 7/015* (2013.01); *H04N 2005/2255* (2013.01)

(58) Field of Classification Search
USPC .............................................. 348/65, 61, 64
See application file for complete search history.

(56) References Cited

U.S. PATENT DOCUMENTS

| | | | |
|---|---|---|---|
| 8,793,724 B2 * | 7/2014 | Robinson | H04N 21/44026 705/51 |
| 9,392,214 B2 * | 7/2016 | Hanovich | H04N 7/0125 |
| 2012/0162401 A1 * | 6/2012 | Melder | H04N 7/183 348/65 |
| 2014/0130083 A1 * | 5/2014 | Robinson | H04N 21/44026 725/31 |

\* cited by examiner

*Primary Examiner* — Paulos M Natnael
(74) *Attorney, Agent, or Firm* — D. Kliger I.P. Services Ltd.

(57) ABSTRACT

Apparatus includes an endoscope including a high definition video camera, and a host processor, which is configured to receive video data encapsulated in a standard definition transmission format, and to store the encapsulated video data in a memory. The apparatus further includes a data converter, which is configured to receive high definition video data originating from an image captured by the high definition video camera as a sequence of packets and to encapsulate the sequence of packets in the standard definition transmission format. The data converter is also configured to convey the encapsulated packets to the host processor so that the host processor stores the packets in the memory.

16 Claims, 8 Drawing Sheets

ENDOSCOPE WITH HIGH DEFINITION VIDEO RECORDER/PLAYER

CROSS-REFERENCE TO RELATED APPLICATION

This application is a division of U.S. patent application Ser. No. 13/760,086, filed Feb. 6, 2013, which is incorporated herein by reference.

FIELD OF THE INVENTION

The present invention relates generally to recording and playing back of high definition video data.

BACKGROUND OF THE INVENTION

A typical high definition video camera may generate a raw video stream of approximately 150 Mbytes or more per second. Handling such high data rates, and storing the extremely large amounts of data generated, typically requires significant computational resources.

A system which reduces the resources needed for operating high definition video would be advantageous.

SUMMARY OF THE INVENTION

An embodiment of the present invention provides apparatus, including:

a host processor, which is configured to receive video data encapsulated in a standard definition transmission format, and to store the encapsulated video data in a memory; and a data converter, which is configured:

to receive high definition video data as a sequence of packets, to encapsulate the sequence of packets in the standard definition transmission format, and to convey the encapsulated packets to the host processor so that the host processor stores the packets in the memory.

Typically, the high definition video data includes compressed high definition video data. The compressed high definition video data may be compressed using at least one of spatial redundancy and temporal redundancy.

In a disclosed embodiment the packets within the sequence are equally sized.

In a further disclosed embodiment the data converter is configured to select a number of packets for encapsulation to be a largest integral number of packets able to fit into a line of the standard definition transmission format.

In a yet further disclosed embodiment the data converter is configured to receive the encapsulated packets in the standard definition transmission format from the host processor, to extract the sequence of packets from the encapsulated packets, and to transmit the sequence of packets as high definition video data. The high definition video data may consist of compressed high definition video data.

In an alternative embodiment the apparatus may also include a codec which is configured to compress the high definition video data as the sequence of packets, and to convert the sequence of packets to video data in a high definition transmission format. The codec may be configured to receive the sequence of packets from the data converter, and to convert the sequence of packets to video data in a high definition transmission format suitable for a screen displaying high definition video.

In a further alternative embodiment the standard definition transmission format includes a preset number of lines of data, and each line of data includes a predetermined number of pixels.

There is further provided, according to an embodiment of the present invention, a method, including:

configuring a host processor to receive video data encapsulated in a standard definition transmission format, and to store the encapsulated video data in a memory; and configuring a data converter:

to receive high definition video data as a sequence of packets, to encapsulate the sequence of packets in the standard definition transmission format, and to convey the encapsulated packets to the host processor so that the host processor stores the packets in the memory.

There is further provided, according to an alternative embodiment of the present invention, apparatus, including:

an endoscope having a high definition video camera;

a host processor, which is configured to receive video data encapsulated in a standard definition transmission format, and to store the encapsulated video data in a memory; and a data converter, which is configured:

to receive high definition video data originating from an image captured by the high definition video camera as a sequence of packets, to encapsulate the sequence of packets in the standard definition transmission format, and to convey the encapsulated packets to the host processor so that the host processor stores the packets in the memory.

There is further provided, according to a further alternative embodiment of the present invention, a method, including:

incorporating a high definition video camera into an endoscope;

configuring a host processor to receive video data encapsulated in a standard definition transmission format, and to store the encapsulated video data in a memory; and configuring a data converter:

to receive high definition video data originating from an image captured by the high definition video camera as a sequence of packets, to encapsulate the sequence of packets in the standard definition transmission format, and to convey the encapsulated packets to the host processor so that the host processor stores the packets in the memory.

The present invention will be more fully understood from the following detailed description of the embodiments thereof, taken together with the drawings in which:

DETAILED DESCRIPTION OF EMBODIMENTS

Overview

An embodiment of the present invention provides an efficient, simple, low-cost system for storing and playing back high definition video data.

In the case of storing, "raw" high definition video in a standard high definition format is typically compressed using spatial and/or temporal redundancy. (An example of high definition video is formed as 1080 lines, 1920 pixels per line, and may be generated by a high definition camera.) The compression is typically performed in a codec, which outputs the high definition video data as a sequence of packets incorporating the video data in a compressed form. Typically, although not necessarily, the packets are equally sized packets of 188 bytes.

A data converter receives the sequence of packets, and encapsulates the packets in the sequence into a standard definition transmission format. Typically the standard definition transmission format defines frames of a preset number of lines, each line being transmitted on a pixel basis. The converter encapsulates the packets (of high definition compressed data) line by line, into the standard definition transmission format, and the data in this form is conveyed to a host processor configured to receive and transmit data in the standard definition transmission format. If, for example, a line of standard definition transmission format data comprises 720 pixels, and there are 2 bytes per pixel, then a "standard" line is 1440 bytes. In this case the converter may incorporate seven of the 188 byte packets (1316 bytes) into a line.

The host processor stores the data received from the converter in a memory buffer coupled to the processor. The data is stored as standard definition frames, and the processor then transfers and stores the data to a non-volatile memory.

For playing back from a memory, the process described above is reversed. In this case the host processor conveys frame data to the data converter. The converter extracts the high definition compressed packets from the standard definition frame data, assembles the extracted packets into a sequence of transport stream packets, and transmits the sequence of packets as high definition video data in a compressed form. The sequence of packets may be transmitted to a codec, which decodes the compressed video to regenerate high definition video in a standard high definition format suitable for display on a high definition screen.

DETAILED DESCRIPTION

Figure 1:
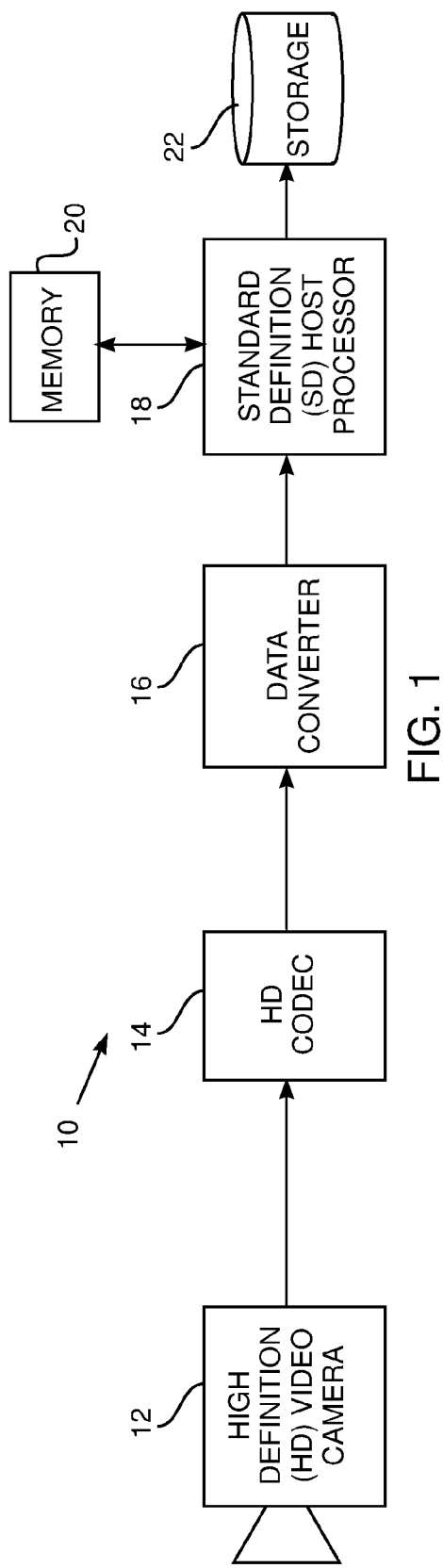
FIG. 1 is a schematic block diagram of components of a high definition (HD) video record/playback system, according to an embodiment of the present invention.

Reference is now made to FIG. 1, which is a schematic block diagram of components of a high definition (HD) video record/playback system 10, according to an embodiment of the present invention. System 10 is able to act both in a recording mode for HD video, as well as in a playback mode for the video. For clarity, the description of system 10 with respect to FIG. 1 assumes that the system is operating in the recording mode.

A high definition video camera 12 generates "raw," i.e., uncompressed, HD video signals according to any HD protocol known in the art. Such a protocol may be that provided in, for example, the SMPTE 274M or SMPTE 296M standards, which are available from The Society of Motion Picture and Television Engineers, 55 West 42d. St., New York 36 N.Y. The raw HD signals have a relatively high bit rate. Consider, for example, a signal where each pixel generated by the camera requires 3 bytes (corresponding to an unfiltered RGB signal), there are 1920 pixels in each line of a picture frame, a frame has 1080 lines, and the camera transmits at 24 frames/s. In this case the camera transmits approximately 150 Mbytes/s, corresponding to approximately 1.2 Gbits/s.

In order to facilitate the management of such large amounts of data, as well as the high bit rates the data requires for real-time operation, the raw data is typically compressed into a compressed format according to a defined protocol. The compression typically uses the fact that there is spatial redundancy within any given frame, and that there is typically temporal redundancy between adjacent frames.

Typically, and as assumed hereinbelow, the compression produces intra-coded pictures (I-frames) which are effectively "stand-alone" sets of signals which fully specify respective scenes. Each I-frame uses spatial redundancy to compress the information of its scene. The compression typically also produces predictive frames (P-frames) and bi-predictive (B-frames). P-frames only use changes from a previous image; B-frames use changes from previous and subsequent images.

System 10 is assumed to use an HD codec (coder-decoder) 14 to code, or compress, the raw HD signals from camera 12 into the types of frames described above. Codec 14 outputs the frames generated as packets of compressed data. Codec 14 may formulate and output the packets of data in any convenient compressed format. By way of example and for clarity, the packets of data produced by codec 14 are assumed to comply with the MPEG-2 standard, available from the International Organization for Standardization (ISO), Geneva, Switzerland. The MPEG-2 standard provides for the packets from codec 14 being output as a packetized elementary stream, each packet in the stream being 188 bytes in length. In one embodiment codec 14 comprises an MB86H55 device, produced by Fujitsu Limited, Tokyo, Japan, which operates according to the MPEG-2 standard. However, the packets of data output by codec 14 may be in any other standard or non-standard format, and those having ordinary skill in the art will be able to adapt the present description, mutatis mutandis for such other formats. The transport stream protocol for the packets may comply with the MPEG-2 protocol, or with any other suitable transport protocol.

System 10 comprises other elements, i.e., a data converter 16, a standard definition video host processor 18, a volatile memory buffer 20, and a non-volatile storage device 22. The functions of the other elements are described below.

Figure 2:
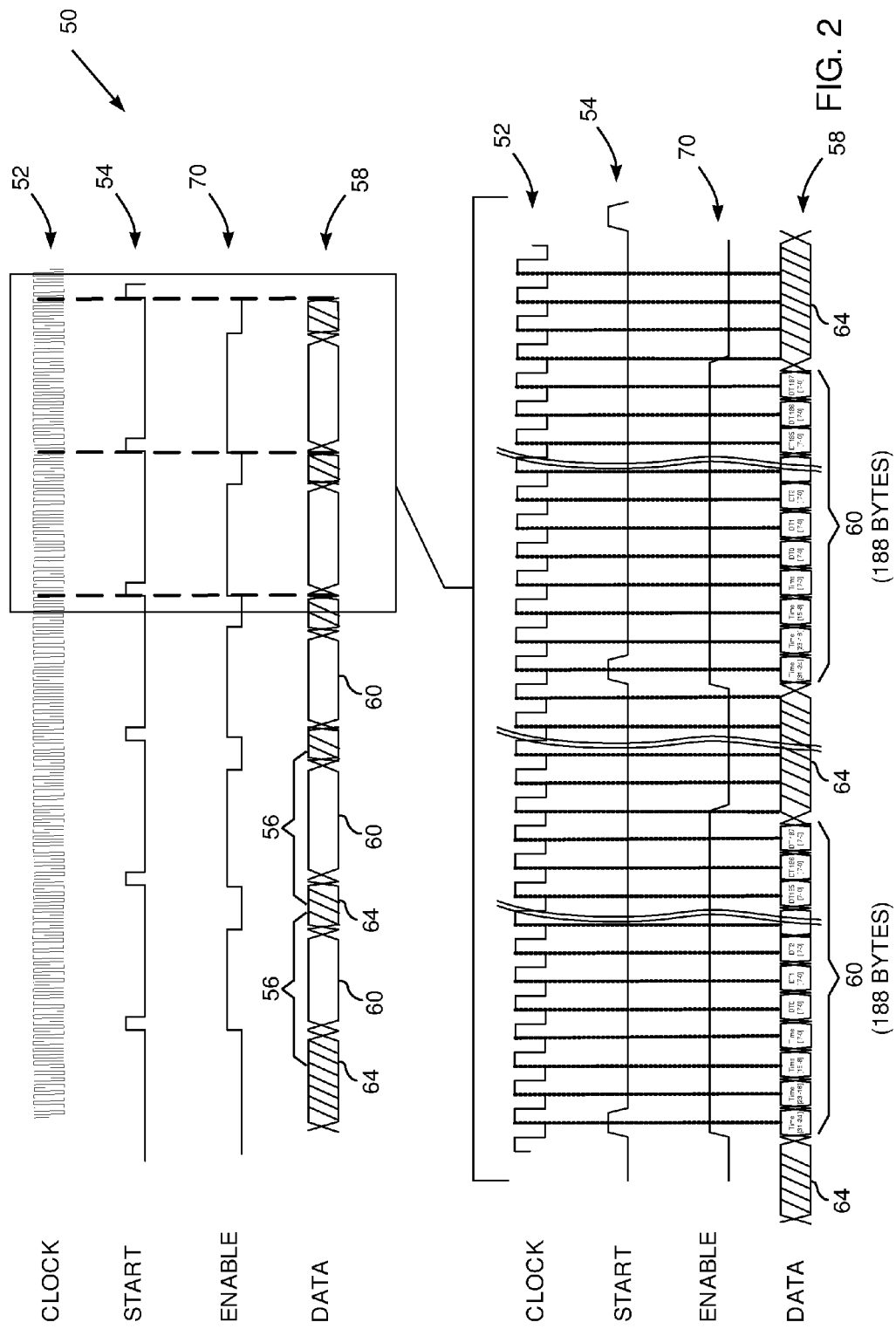
FIG. 2 is a simplified timing diagram for a codec, according to an embodiment of the present invention.

FIG. 2 is a simplified timing diagram 50 for codec 14, according to an embodiment of the present invention. Codec 14 operates using a clock signal 52, which is typically approximately 27 MHz, or a higher frequency up to 54 MHz. Signal 52 may be generated internally to the codec, or an external clock may be used. For simplicity, in the description herein the clock signal is assumed to be generated within codec 14 at 27 MHz, such as is provided within the MB86H55 referred to above, and the clock is assumed to be provided to the other elements of system 10 as required. A start signal 54 indicates the beginning of respective valid data, in the form of packets 60, and valid data for the packets is defined by an enable signal 70. Packets 60 comprise compressed data, and are assumed herein, by way of example, to be 188 bytes in size. However, embodiments of the present invention are not limited to a specific size of packet, or to having the packets equal in size.

Each 188 byte packet 60 is preceded and followed by invalid data 64. Invalid data 64 acts to encapsulate a given compressed data packet 60 within a given data group 56. The codec transmits the data, comprising compressed data packets 60 and invalid data 64, in the form of a data signal 58.

Figure 3:
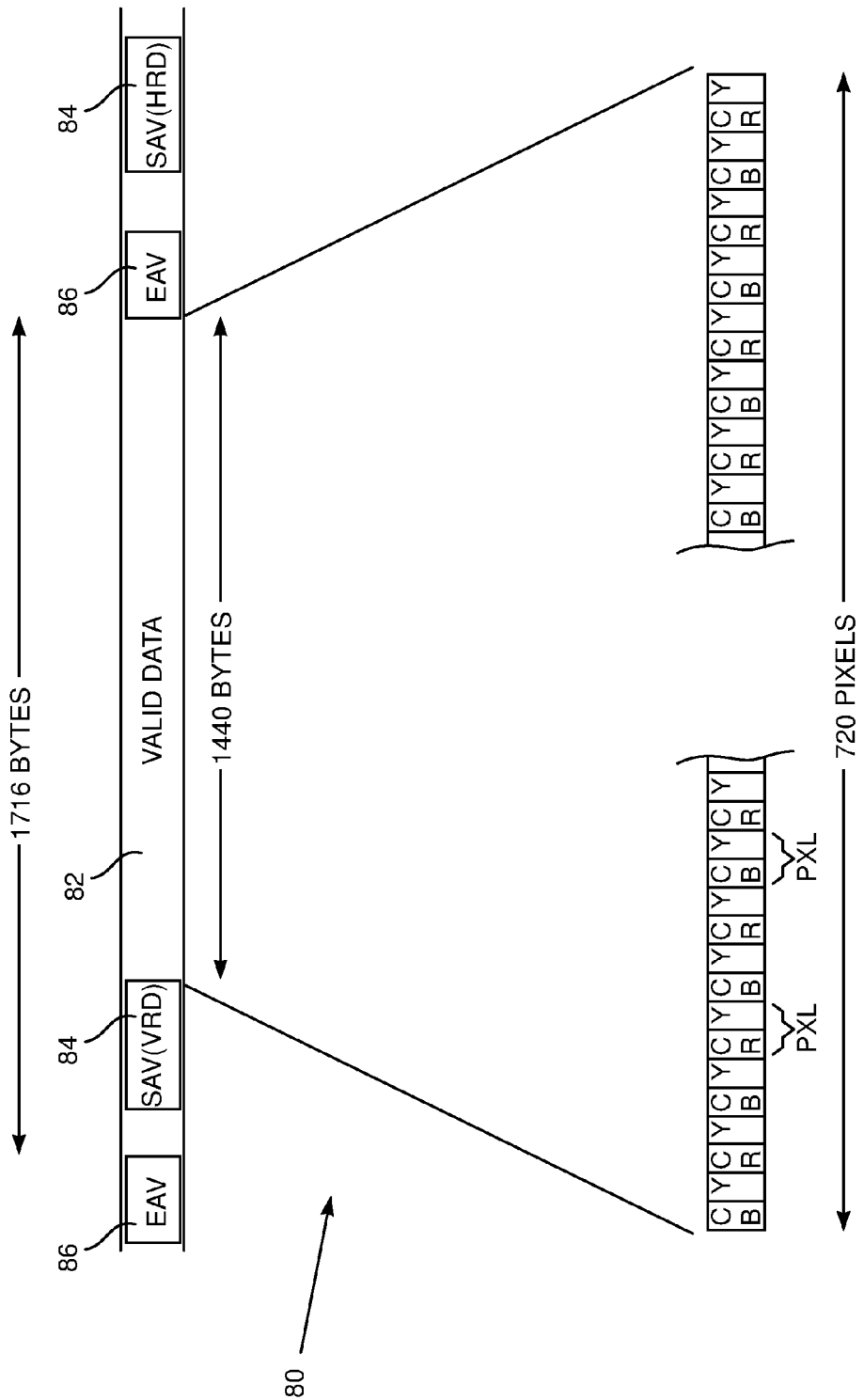
FIG. 3 is a simplified timing diagram for a standard definition video host processor, according to an embodiment of the present invention.

FIG. 3 is a simplified timing diagram 80 for standard definition video host processor 18 (FIG. 1), according to an embodiment of the present invention. Standard definition video processor 18 is configured to receive and store uncompressed video frames transmitted to the processor on a pixel basis in a standard definition video format. In one embodiment video processor 18 comprises a DM335 device produced by Texas Instruments, of Dallas, Tex.

Processor 18 receives successive frames of pixels, each frame being transmitted on a line by line basis. By way of example, in the description herein the format of the standard definition video received by processor 18 is assumed to comply with an ITU-R Recommendation BT.656 protocol (ITU 656) for uncompressed video, provided by the International Telecommunication Union (ITU), Geneva, Switzerland. Inter alia, ITU 656 provides for uncompressed video data transferred in a 4:2:2 color space format, where each pixel is composed of two bytes: a luma (Y) byte, and alternating brightness chrominance (CB) and color chrominance (CR) bytes. Such a transmission mode is assumed herein.

However, as will be appreciated from the description herein, in embodiments of the present invention host processor 18 may be configured to receive and store video signals in substantially any standard or non-standard format, so long as the data received is in an uncompressed format defining the video on a pixel basis. Such formats include, but are not limited to: 4:4:4, 4:4:0, 4:2:0, 4:1:1, and 4:1:0, all of which formats are known in the video art. All of these formats, except the 4:4:4 format, use less than three bytes to define a pixel; the 4:4:4 format uses three bytes to define a pixel.

Diagram 80 illustrates a single line 82 of data formatted according to the ITU 656 protocol. Each line 82 begins with a start of active video (SAV) precursor set of bytes 84, and finishes with an end of active video (EAV) terminator set of bytes 86. SAV 84 acts as a line, or horizontal sync, delineator, by incorporating a horizontal distance (HRD) set of bytes in each SAV. As stated above, processor 18 receives successive frames of pixels on a line by line basis. Consequently, as required, an SAV may also act as a frame delineator, by incorporating a vertical distance (VRD), or vertical sync, set of bytes in appropriate SAVs.

Consider, for example, if the uncompressed video comprises frames of 720 pixels/line×480 lines/frame. A frame of 720 pixels×480 lines corresponds to one of the NTSC (National Television System Committee) standards. In this case each frame of 480 lines begins with an SAV having a VRD set of bytes, and each of the remaining 479 lines in the frame begins with an SAV having an HRD set of bytes. As illustrated in diagram 80, for the 4:2:2 format described above, there are 1440 bytes of valid data per line, defining 720 pixels per line.

There is no requirement that the data received by host processor 18 is according to any specific television standard, such as an NTSC standard referred to above. For example, the data may be according to a PAL (phase alternating line) standard, or a variation on a PAL standard. (The NTSC and PAL standards are available from the ITU.) However, the data received by host processor 18 may be according to any other standard transmitting uncompressed video data that is known in the art.

Figure 4:
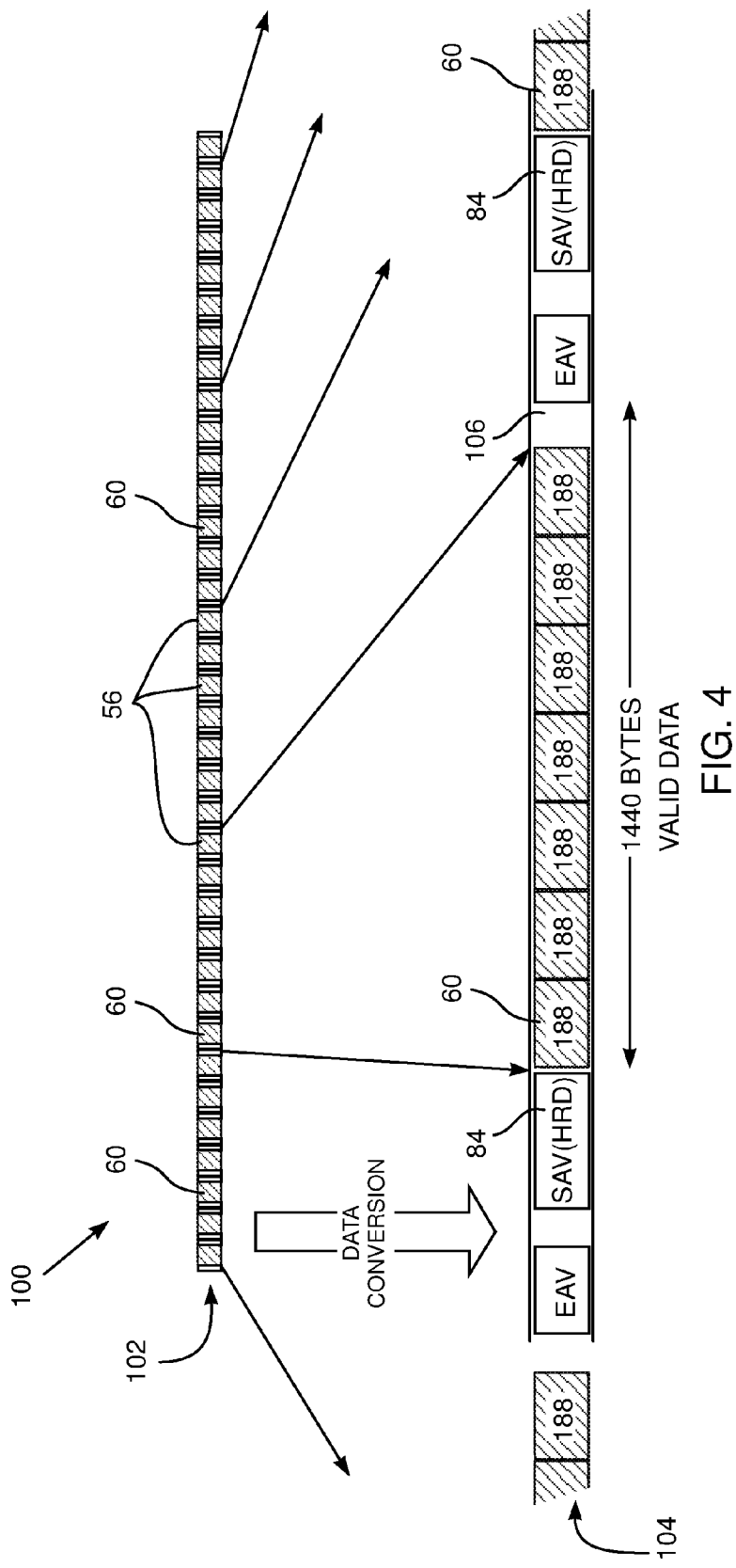
FIG. 4 is a schematic diagram illustrating the data format conversion performed by a data converter, according to an embodiment of the present invention.

FIG. 4 is a schematic diagram 100 illustrating the data format conversion performed by data converter 16 (FIG. 1), according to an embodiment of the present invention. In one embodiment converter 16 is implemented as a field programmable gate array (FPGA), although other modalities for implementing the converter will be familiar to those having ordinary skill in the art, and all such modalities are assumed to be comprised within the scope of the present invention.

Converter 16 is configured to receive data groups 56, as a continuous input data stream 102, from codec 14. From each group 56, the converter extracts the respective 188 byte data packet 60. As each packet is extracted, it is assembled into an output data stream 104. Data stream 104 is configured to be consistent with the standard definition video format receivable by standard definition processor 18. Converter 16 performs the assembly by removing invalid data 64 (FIG. 2), surrounding each data packet 60. The converter then assembles the 188 byte data packets into data stream 104.

Converter 16 configures the assembled 188 byte data packets of data stream 104 to be encapsulated so that the data stream is consistent with the standard definition video format receivable by standard definition processor 18. As explained above with reference to FIG. 3, such a data stream comprises sequences of 1440 bytes of valid data, each group of 1440 bytes being preceded by an SAV set of bytes and having an EAV set of bytes after the group.

Thus, converter 16 formulates each group of 1440 bytes to include at least one 188 byte packet. Typically the number of 188 byte packets incorporated into a "line" of the standard definition video format is the largest integral number of packets that fit into the line. Thus, in the example illustrated in FIG. 4, the converter assembles seven 188 byte packets into the 1440 byte valid data section, leaving a "space" 106 of 1440−(7×188)=124 bytes in the valid data section. Seven is the largest number of 188 byte packets that fit into a 1440 byte line. Converter 16 may populate space 106 with any convenient values, such as all zeros. Converter 16 formulates succeeding lines of data stream 104 to have the same structure as the example illustrated in FIG. 4, i.e., seven 188 byte packets and a space of 124 bytes. In order to comply with the standard for data into processor 18, wherein the data is transmitted as frames, converter applies frame delineators SAV(VRD) as appropriate to data stream 104.

The data conversion example illustrated in FIG. 4 is but one example of how 188 byte data packets from codec 14 may be assembled by converter 16 into a form suitable for standard definition processor 18. Other assemblages, of a form suitable for processor 18, will be apparent to those having ordinary skill in the art. For example, rather than leaving space 106 unused, an alternative embodiment may populate at least part of space 106 with part of an eighth 188 byte packet. The remainder of the eighth 188 byte may be used as the first data in a succeeding "line" of data, and the succeeding line may have seven complete 188 byte packets. All such assemblages, wherein complete or partial 188 byte packets are formed by a data conversion process into a form suitable for standard definition processor 18, are assumed to be comprised within the scope of the present invention.

Figure 5:
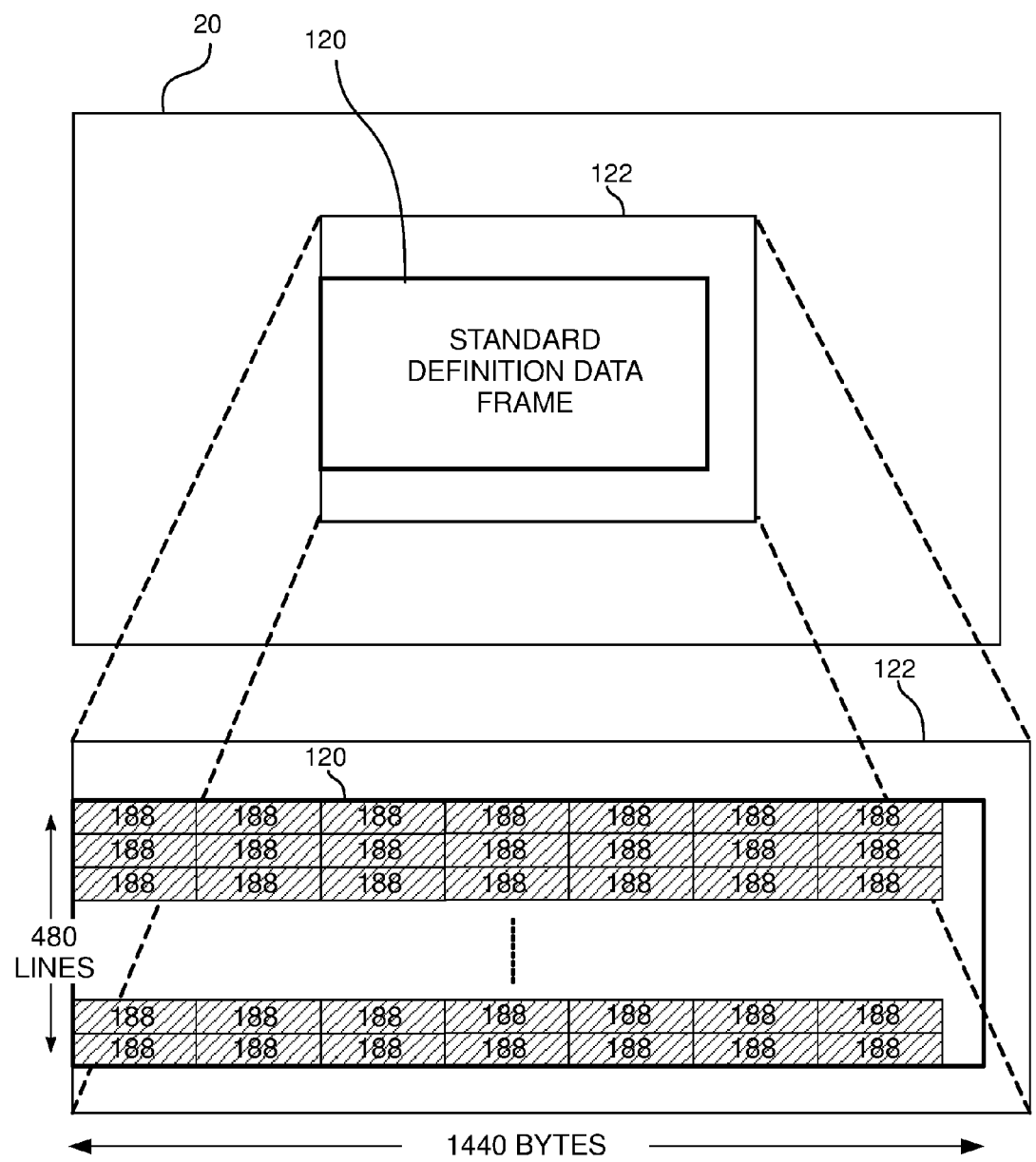
FIG. 5 is a schematic diagram illustrating a format in which a processor stores data in a volatile memory, according to an embodiment of the present invention.

FIG. 5 is a schematic diagram illustrating a format in which processor 18 stores data in volatile memory buffer 20 (FIG. 1), according to an embodiment of the present invention. The processor typically stores the data in non-volatile memory 22 in an encapsulated format, for example, in a video file container format. The data received as data stream 104 by processor 18 is stored in memory buffer 20 as frames of standard definition data. Thus, in the case of data stream 104 transmitting frames of 480 lines, each line comprising 1440 bytes (720 pixels) of data, processor stores each frame as a valid data frame 120. For illustration purposes valid data frame 120 is shown as a two-dimensional array; however, data frame 120 may be stored in any format suitable for memory 20, so long as the data may be retrieved from the memory in the two-dimensional format illustrated.

Typically, valid data frame 120 is encapsulated within a global frame 122. Storage of valid data frame 120 in a standard definition format, such as the 480 lines×720 pixels format exemplified above, enables any standard definition monitor to display the frames sequentially. However, while such a display is possible, and the frames displayed will indeed show as 480 lines, each line having 720 pixels, it will be understood that no intelligible information will display. Each pixel displayed is generated from two bytes of a 188 byte packet, and the 188 byte packet is compressed high definition video. The scene visible on the standard definition monitor will consequently appear as noise.

Figure 6:
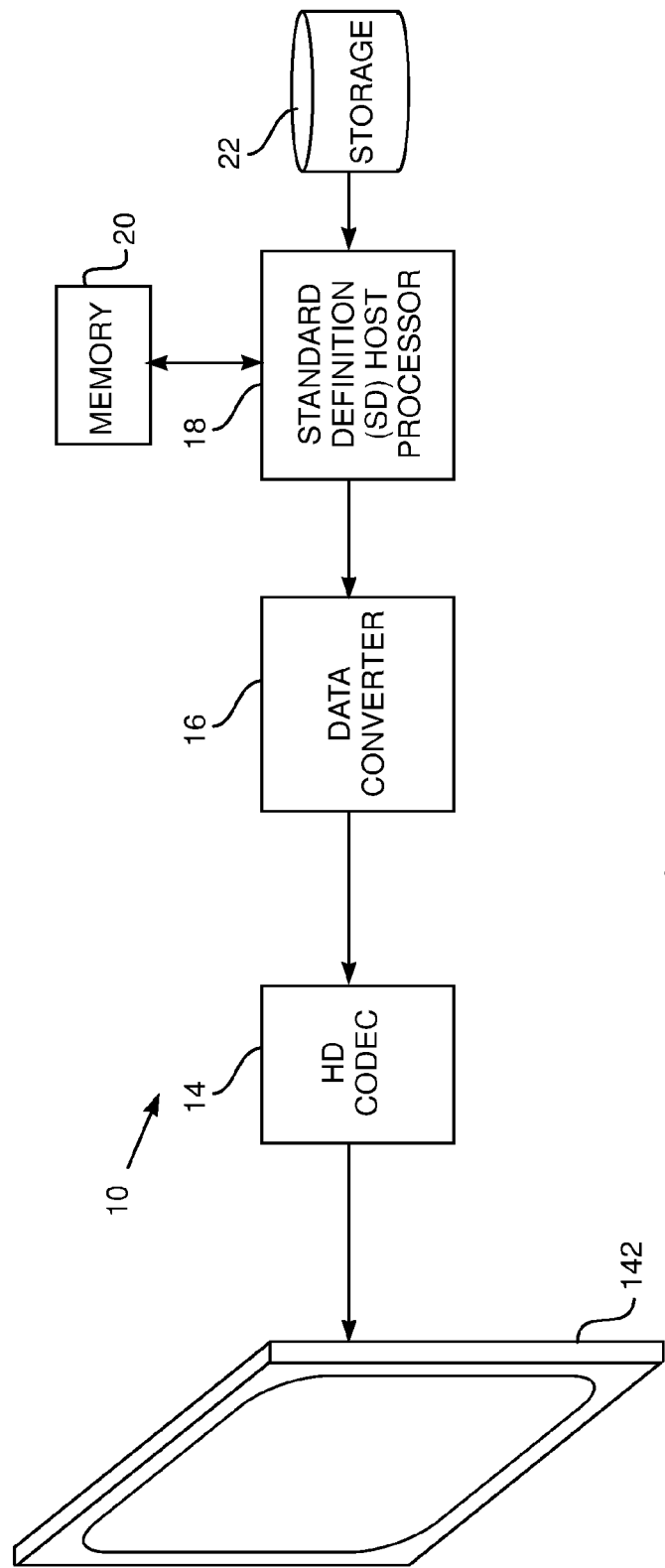
FIG. 6 is a schematic block diagram of the system of FIG. 1 operating in a playback mode, according to an embodiment of the present invention.
Figure 7:
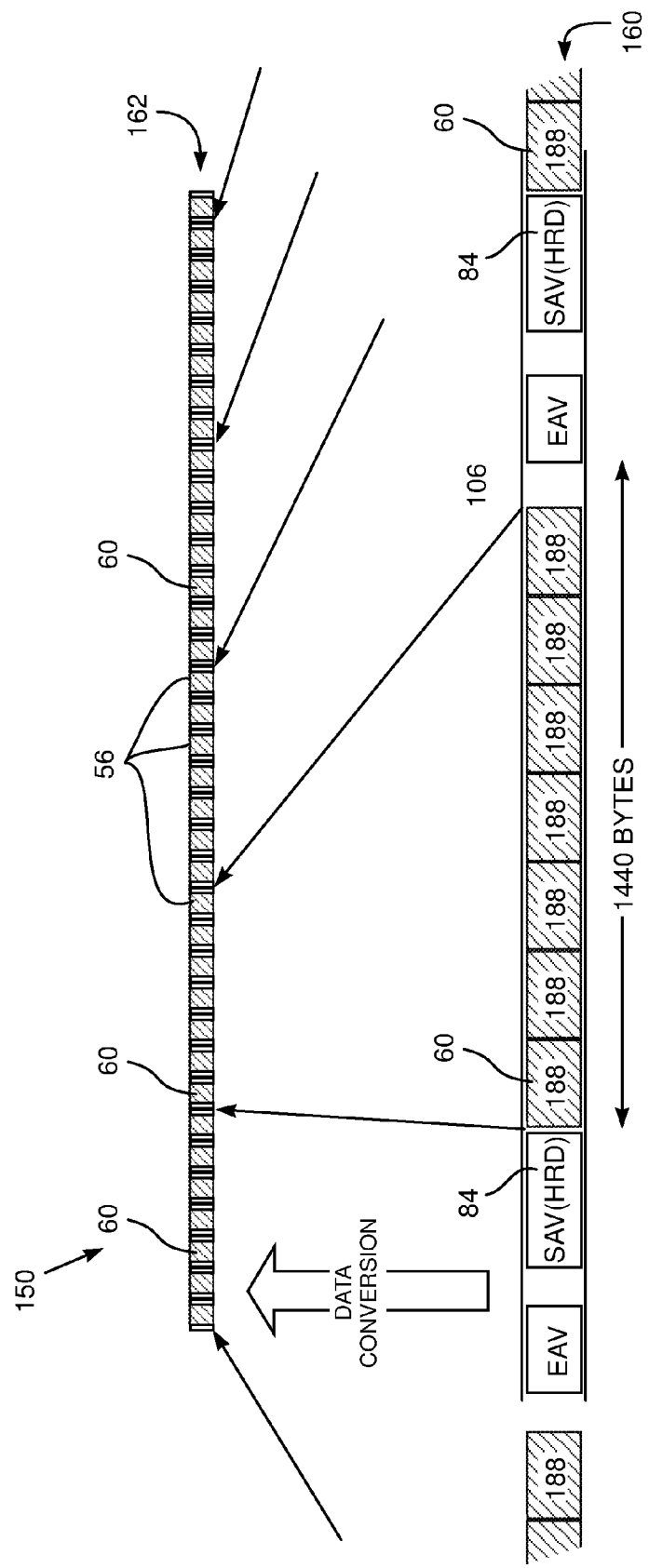
FIG. 7 is a schematic diagram illustrating the data format conversion performed by the data converter when the system of FIG. 1 operates in the playback mode, according to an embodiment of the present invention.

FIG. 6 is a schematic block diagram of system 10 operating in a playback mode, and FIG. 7 is a schematic diagram 150 illustrating the data format conversion performed by data converter 16 (FIG. 1) when system 10 operates in the playback mode, according to embodiments of the present invention. The operation of system 10 in the playback mode is generally similar to the operation of the system in the recording mode (FIGS. 1-5), except that, as explained in more detail below, the functions performed by elements operating in system 10 are generally reversed from the functions performed by the elements operating in the recording mode. In the playback mode, video in a high definition format displays on a high definition screen 142.

As illustrated in FIG. 6, in the playback mode processor 18 may receive data indirectly from non-volatile memory 22, or directly from volatile memory buffer 20. If data is received from non-volatile memory 22, it is initially stored in volatile memory buffer 20 in the format described with reference to FIG. 5, i.e., the data is in the form of standard definition frames. In the case exemplified in FIG. 5, each frame of data comprises 480 lines, and each line comprises 1440 bytes (representing 720 pixels). Processor 18 transmits the standard definition data in a standard definition format described herein, and the data is received by data converter 16. The DM335 device referred to above is configured to be able to transmit standard definition data from a memory such as memory buffer 20 in the standard definition format described herein.

As illustrated in FIG. 7, the standard definition data transmitted from processor 18 is in the form of a data stream 160. In a data conversion process that is the reverse of the process followed by data converter 16 and that is described above with reference to FIG. 4, the data converter extracts 188 byte packets 60 from data stream 160, and assembles the packets into a stream 162 of packets of high definition compressed video data. Data stream 160 has substantially the same format as data stream 104, and data stream 162 has substantially the same format as data stream 102 (FIG. 4), so that elements indicated by the same reference numerals FIGS. 4 and 7 are generally similar in structure and in function.

Returning to FIG. 6, HD Codec 14 receives data stream 162, and decodes, or decompresses, the sequence of 188 byte packets into video in a high definition format, such as is prescribed by the SMPTE 274M or SMPTE 296M standards referred to above, or in another suitable high definition format. The decoding performed by codec 14 is substantially the reverse of the coding process described above with reference to FIGS. 1 and 2. The decoded data is transmitted to screen 142 which displays the data as high definition video.

Figure 8:
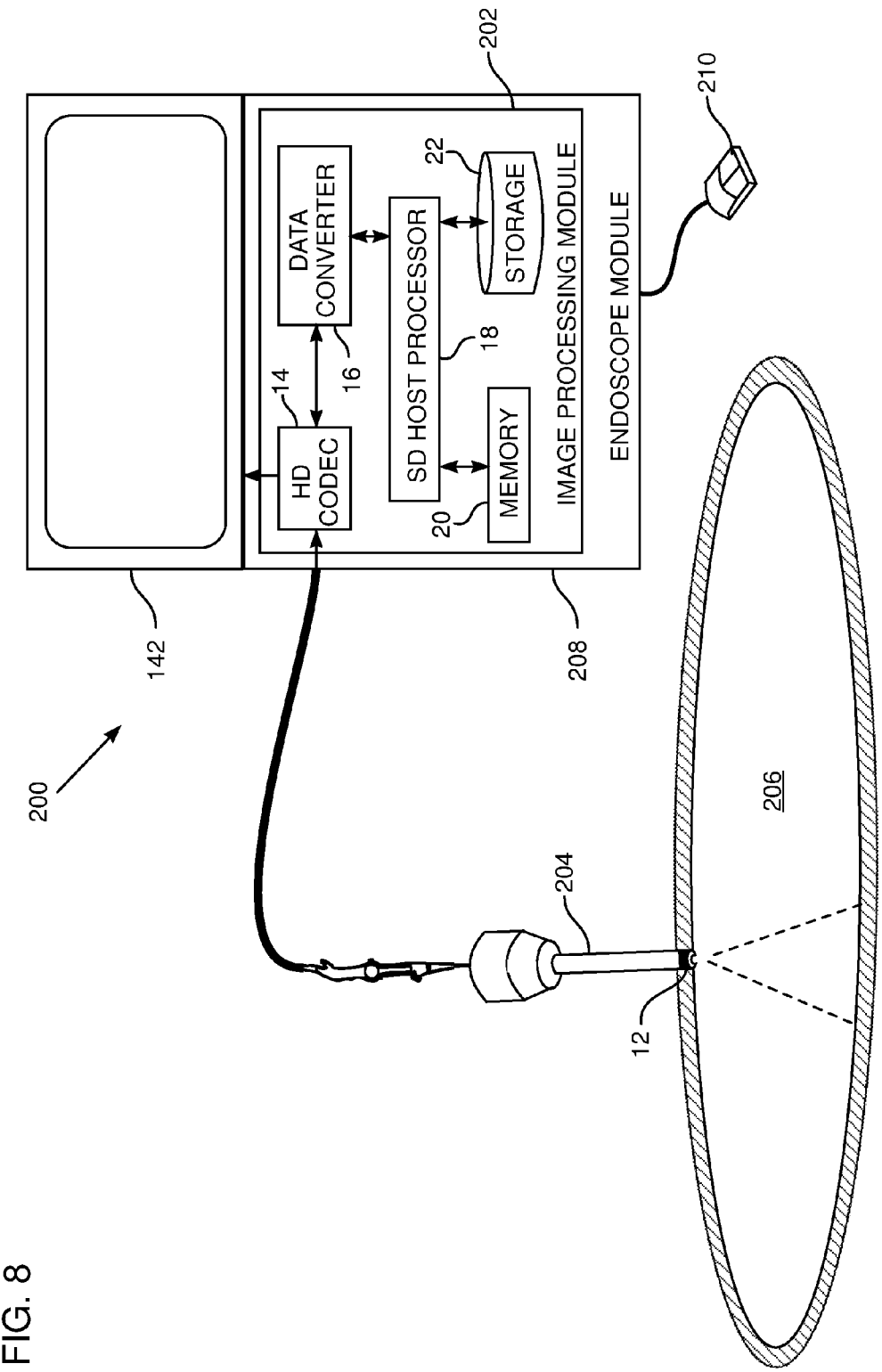
FIG. 8 is a schematic diagram illustrating application of the system of FIG. 1 during a medical procedure, according to an embodiment of the present invention.

FIG. 8 is a schematic diagram illustrating application of video record/playback system 10 in an apparatus 200 used in a medical procedure, according to an embodiment of the present invention. Elements of system 10 are assumed to be comprised in an image processing module 202 and in an endoscope 204 of the apparatus, and apart from the differences described below, the operation of the elements in module 202 and endoscope 204 are generally similar to that of system 10. Thus, elements indicated by the same reference numerals in apparatus 200 and in system 10, in FIGS. 1 and 6, are generally similar in construction and in operation. In apparatus 200, image processing module 202 comprises HD codec 14, data converter 16, standard definition video host processor 18, volatile memory buffer 20, and non-volatile storage device 22.

Apparatus 200 comprises endoscope 204, wherein is installed high definition video camera 12, and the endoscope is assumed use the camera to capture images of a body cavity 206. A professional conducting the medical procedure operates endoscope 204 via an endoscope module 208, which comprises image processing module 202, and high definition video screen 142 is coupled to the endoscope module. The professional uses screen 142 and controls for endoscope module, typically a pointing device such as a mouse 210, to operate the endoscope during the procedure.

During the procedure, the images captured by camera 12 are stored in volatile memory buffer 20 and in non-volatile memory storage device 22, substantially as described above with reference to FIGS. 1-5. During the procedure the images may also be viewed on screen 142.

Once the images have been stored in device 22, they may be played back to screen 142, substantially as described above with reference to FIGS. 6 and 7.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus, comprising:
   an endoscope comprising a high definition video camera;
   a host processor, which is configured to receive video data encapsulated in a standard definition transmission format, and to store the encapsulated video data in a memory;
   a data converter, which is configured:
   to receive high definition video data originating from an image captured by the high definition video camera as a sequence of packets, to encapsulate the sequence of packets in the standard definition transmission format, and to convey the encapsulated packets to the host processor so that the host processor stores the packets in the memory; and a codec which is configured to compress the high definition video data as the sequence of packets, and to convert the sequence of packets to video data in a high definition transmission format, wherein the codec is configured to receive the sequence of packets from the data converter, and to convert the sequence of packets to video data in a high definition transmission format suitable for a screen displaying high definition video.

2. The apparatus according to claim 1, wherein the high definition video data comprises compressed high definition video data.

3. The apparatus according to claim 2, wherein the compressed high definition video data is compressed using at least one of spatial redundancy and temporal redundancy.

4. The apparatus according to claim 1, wherein the packets within the sequence are equally sized.

5. The apparatus according to claim 1, wherein the data converter is configured to select a number of packets for encapsulation to be a largest integral number of packets able to fit into a line of the standard definition transmission format.

6. The apparatus according to claim 1, wherein the data converter is configured to receive the encapsulated packets in the standard definition transmission format from the host processor, to extract the sequence of packets from the encapsulated packets, and to transmit the sequence of packets as high definition video data.

7. The apparatus according to claim 6, wherein the high definition video data comprises compressed high definition video data.

8. The apparatus according to claim 1, wherein the standard definition transmission format comprises a preset number of lines of data, and wherein each line of data comprises a predetermined number of pixels.

9. A method, comprising:
incorporating a high definition video camera into an endoscope;
configuring a host processor to receive video data encapsulated in a standard definition transmission format, and to store the encapsulated video data in a memory;
configuring a data converter:
to receive high definition video data originating from an image captured by the high definition video camera as a sequence of packets,
to encapsulate the sequence of packets in the standard definition transmission format, and
to convey the encapsulated packets to the host processor so that the host processor stores the packets in the memory; and
configuring a codec to compress the high definition video data as the sequence of packets, and to convert the sequence of packets to video data in a high definition transmission format,
wherein the codec is configured to receive the sequence of packets from the data converter, and to convert the sequence of packets to video data in a high definition transmission format suitable for a screen displaying high definition video.

10. The method according to claim 9, wherein the high definition video data comprises compressed high definition video data.

11. The method according to claim 10, wherein the compressed high definition video data is compressed using at least one of spatial redundancy and temporal redundancy.

12. The method according to claim 9, wherein the packets within the sequence are equally sized.

13. The method according to claim 9, wherein the data converter is configured to select a number of packets for encapsulation to be a largest integral number of packets able to fit into a line of the standard definition transmission format.

14. The method according to claim 9, wherein the data converter is configured to receive the encapsulated packets in the standard definition transmission format from the host processor, to extract the sequence of packets from the encapsulated packets, and to transmit the sequence of packets as high definition video data.

15. The method according to claim 14, wherein the high definition video data comprises compressed high definition video data.

16. The method according to claim 9, wherein the standard definition transmission format comprises a preset number of lines of data, and wherein each line of data comprises a predetermined number of pixels.

* * * * *